United States Patent
Gemunder et al.

(10) Patent No.: US 6,522,086 B2
(45) Date of Patent: Feb. 18, 2003

(54) PHOTO CURING LIGHT SYSTEM HAVING MODULATED LIGHT INTENSITY CONTROL

(75) Inventors: Elliot R. Gemunder, Dix Hills, NY (US); Hyeok-Jae Chi, Wheeling, IL (US)

(73) Assignee: Air Techniques, Inc., Hicksville, NY (US)

(*) Notice: Subject to any disclaimer, the term of this patent is extended or adjusted under 35 U.S.C. 154(b) by 0 days.

(21) Appl. No.: 09/861,735

(22) Filed: May 21, 2001

(65) Prior Publication Data

US 2002/0014864 A1 Feb. 7, 2002

Related U.S. Application Data

(60) Provisional application No. 60/206,584, filed on May 25, 2000.

(51) Int. Cl.[7] ................................................. G05F 1/00
(52) U.S. Cl. ..................... 315/291; 315/292; 315/148; 315/158; 250/900; 250/904
(58) Field of Search ................................. 315/291, 292, 315/149, 151, 158; 250/900, 904

(56) References Cited

U.S. PATENT DOCUMENTS

| | | | | |
|---|---|---|---|---|
| 4,697,122 A | * | 9/1987 | Hoffer | 315/158 |
| 5,912,470 A | * | 6/1999 | Eibofner et al. | 250/504 H |
| 6,079,861 A | * | 6/2000 | Woodward et al. | 362/552 |
| 6,118,521 A | * | 9/2000 | Jung et al. | 356/73 |

* cited by examiner

*Primary Examiner*—Don Wong
*Assistant Examiner*—Tuyet T. Vo
(74) *Attorney, Agent, or Firm*—Louis E. Marn; Clifford G. Frayne

(57) ABSTRACT

A photo-curing light system in which a modulation of the light intensity or output is controlled via an analogue control voltage to the control line output of the lamp power supply. The control signal results in the lamp current being reduced from its maximum value to a lower value on a continuous and repeated basis thereby modulating the light and reducing the heating value to surrounding material such as tooth structure during the curing process.

5 Claims, 3 Drawing Sheets

PHOTO CURING LIGHT SYSTEM HAVING MODULATED LIGHT INTENSITY CONTROL

RELATED APPLICATIONS

This application claims the benefit of the filing date of provisional application 60/206,584, filed May 25, 2000.

BACKGROUND OF THE INVENTION

1. Field of the Invention

The present invention relates to photo-curing light systems for photosensitive compounds and more particularly to a photocuring light system having the ability to modulate light intensity.

2. Description of the Prior Art

There are numerous substances which are sensitive to light energy. One class of such substances are characterized by undergoing polymerization in response to applied light energy. This class of substances includes composites and adhesives that have found use in the dental arts with respect to tooth repair or the fabrication of dental prosthetics.

It is known that the time it takes to cure a photosensitive composite or adhesive is influenced by several factors. One is the type of composite or adhesive and the amount required for the application, a second is the intensity of the light energy delivered to the composite or adhesive in order to effectuate the cure of a composite or adhesive and a third is the time duration of exposure.

The typical light source in a high speed dental curing light is a Xenon arc lamp. The lamp's spectral output extends from the ultraviolet (UV) to the infrared (IR). Filters are generally utilized in the optical path to reduce the deleterious heating effects from the infrared (IR). Further filtering is added to match the spectral response of the photo-initiators in the chemical compounds, (e.g. adhesives or composites) utilized in the dental procedures. The most common photo initiator is camphorquinone which has an absorption band in the visible spectrum with a peak of nominally 470 nm.

Typically, plasma arc curing lamps, such as a Xenon arc lamp have filtered spectral output ranges from 430 nm to 500 nm which matches the majority of the camphorquinone absorption band. In certain situations, other photo-initiators are utilized and in such instances with alternative photo-initiators, the absorption band shifts. For instance when the photo-initiator phenyl propanedione is utilized, it has a spectral peak at nominally 420 nm. Therefore the spectral range of the curing lamp must be expanded to cover this absorption band and this expansion of the absorption band may intrude into the ultraviolet spectrum. Expansion into a wider spectral output range results in additional photonic heating to the tooth structure adjacent to dental procedure. It is therefore desirable to be able to cure the desired chemical compounds (e.g. adhesives or composites) in a dental situation regardless of the photo-initiator utilized in the chemical compound while minimizing the increased heating. Applicant is able to accomplish this desired result by modulating the light output of the arc lamp.

OBJECTS OF THE INVENTION

An object of the present invention is to provide for a novel photo-curing system operable in a wider light spectrum.

A further object of the present invention is to provide for a novel photo-curing light system which can accommodate a plurality of photo-initiators having a variety of absorption bands.

A still further object of the present invention is to provide for a novel photo-curing light system which reduces additional heating to the tooth structure when operating in a wider spectral range.

Still further, an object of the present invention is to provide for a novel photo-curing light system by modulating the light intensity or output to reduce the heating factor.

SUMMARY OF THE INVENTION

A photo-curing light system in which modulation of the light intensity or output of the arc lamp is controlled via an analog control voltage to the control line output of the lamp power supply. The analog control voltage is digitally generated by a microprocessor and is converted to an analog signal with the use of a digital to analog converter integrated circuit feeding a constant current circuit using an operational amplifier integrated circuit. The control signal results in the lamp current being reduced from its maximum program value to a lower value. The proportion of the time that the lamp current is high divided by the total time period of the lamp current output is defined as the duty cycle. The amount of heat reduction is proportional to the duty cycle such that the lower the duty cycle, the lower the temperature rise in the tooth structure.

BRIEF DESCRIPTION OF THE DRAWINGS

These and other objects of the present invention will become apparent particularly when taken in light of the following illustrations wherein.

DETAILED DESCRIPTION OF THE INVENTION

Figure 1:
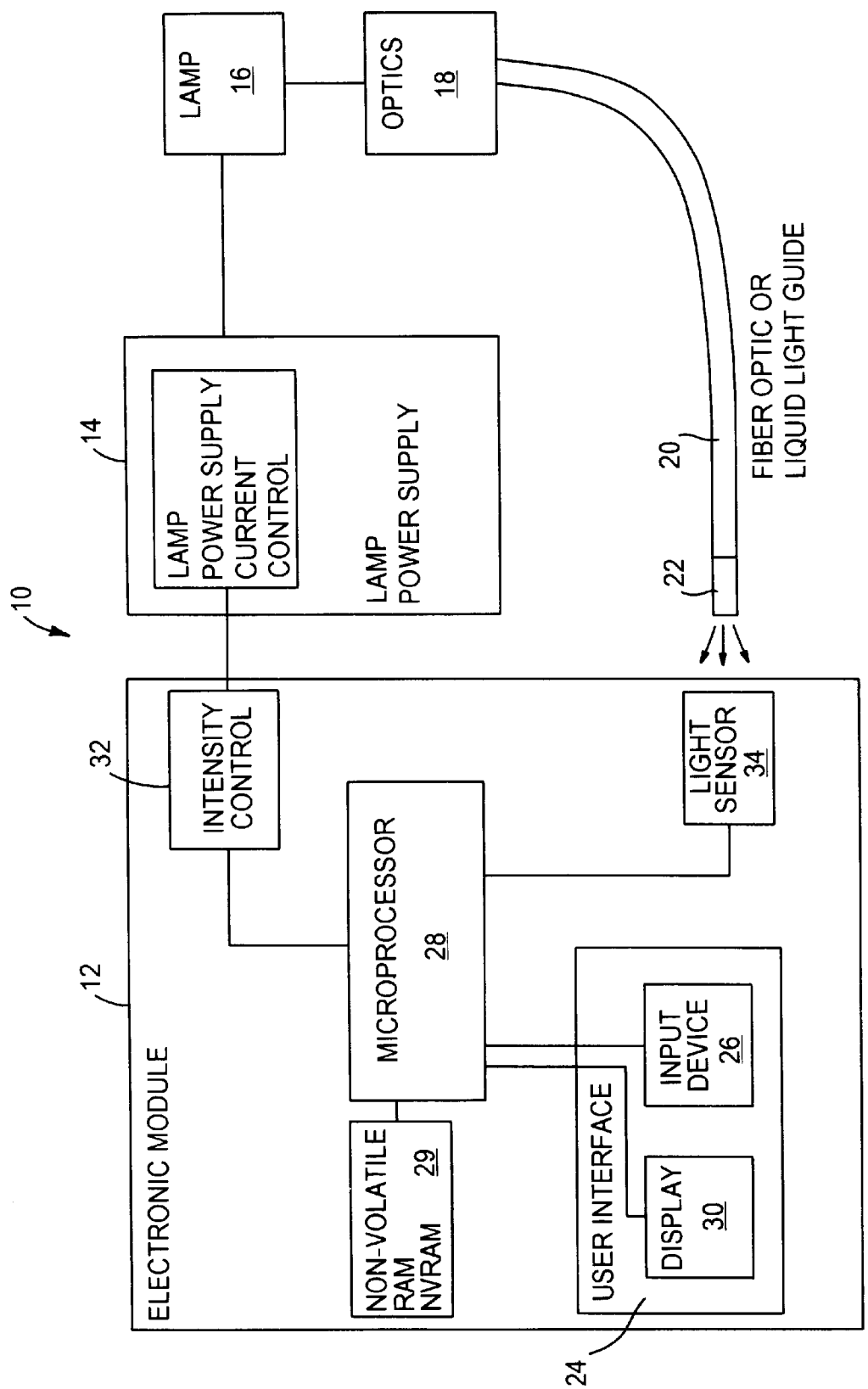
FIG. 1 is a block diagram of the photo-curing light system.

The photo-curing light system 10 of the present invention is illustrated in FIG. 1 and comprises an electronic module 12, a lamp power supply module 14, a lamp 16, and an optics module 18. These modules are positioned within a housing which would be positioned proximate to the dentist chair upon which a patient might recline. The illumination from the lamp 16 is spectrally modified by means of optics module 18 and then transmitted to the tooth structure upon which the dental work is being performed. The transmission of the light is accomplished by means of a fiber optic or liquid core light guide 20 terminating in a curing tip 22 which is positioned within a dental hand piece.

The electronic module 12 of the photo-curing light system 10 is comprised of a micro-processor 28 which is in communication with a user interface 24, including an input pad 26 upon which the dentist or dental technician enters light intensity data and/or time duration data. A display device 30 displays the time and/or intensity.

In operation, when the modulated light mode is selected, the inputted data via input pad 26 is communicated to micro-processor 28 and thence to an intensity control module 32 which in turn controls the lamp power supply 14 and the amount of current transmitting to lamp 16 in order to obtain the intensity selectively inputted via input pad 26. The optics module 18 would contain the various filters presently used to reduce the heating effects from the infrared (IR). This unit may also include a memory chip 29 and a light sensor 34 for calibration.

Figure 2:
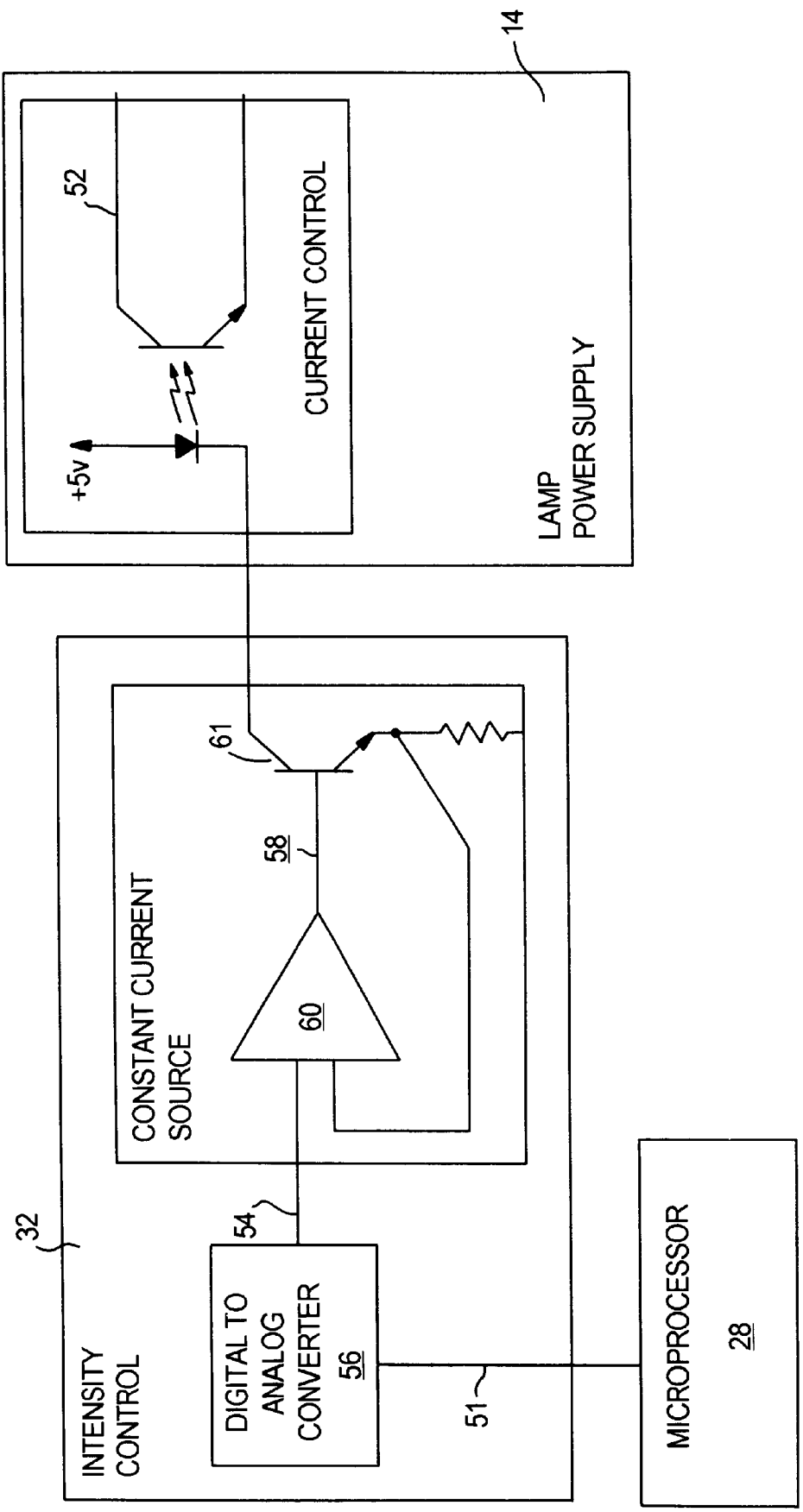
FIG. 2 is a block diagram of the circuitry for modulation of intensity.

FIG. 2 illustrates the control mechanism for the lamp intensity. This circuitry provides for modulation of the light and thus the reduced heating effect when operating in a wider spectral range. The modulation is achieved by controlling the lamp current via an analog control voltage to the control line input of the lamp power supply. Micro-processor 28 generates a digital signal 51 which is then converted to an analog signal by means of a digital to analog converter integrated circuit 56. The analog signal 54 is in communication with a constant current circuit 58 having an amplifier integrated circuit 60 and transistor 61. The analog control signal 54 results in the lamp current 52 being reduced from its maximum program value to a lower value on a continuous and repeated basis resulting in modulation of the light output.

The ratio of the time that the lamp current is at its maximum divided by the total time period of maximum and low lamp current (e.g. total exposure time) is defined as the duty cycle. Control of the duty cycle is also available through the user interface. The lower the duty cycle, the lower the temperature rise in the surrounding tooth structure. Control of modulation is achieved by adjusting the duty cycle and total time period to ensure that the lamp out put has sufficient time to reach its maximum and minimum light levels.

Figure 3:
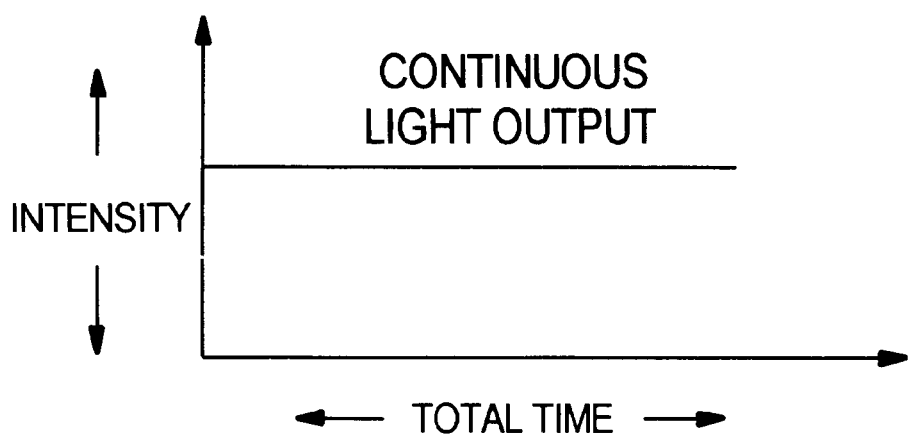
FIG. 3 illustrates the wave shape of a photo-curing light system of the prior art.
Figure 4:
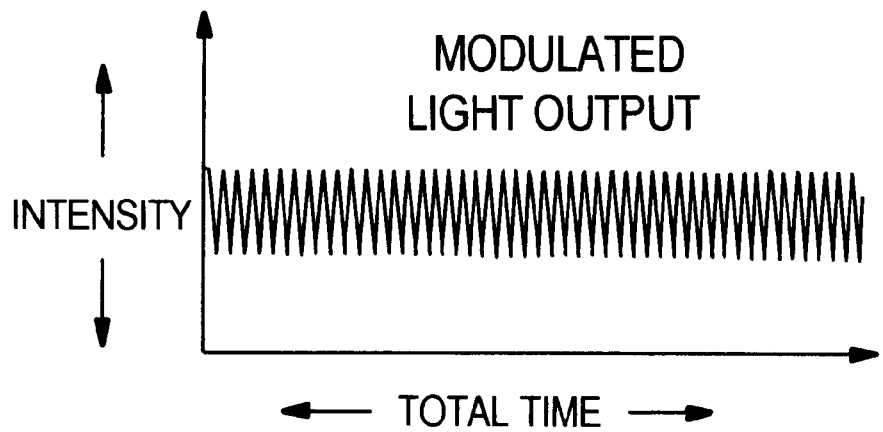
FIG. 4 illustrates the wave shape of a modulated light intensity of the present invention.

FIG. 3 is a graph illustrating the present state of the art with a continuous light output at a particular intensity for a particular time period. FIG. 4 is a graph illustrating a lamp in which the intensity is modulated in accordance with the teachings herein. Clinical tests at the School of Dentistry of a leading University have shown that reduction of the duty cycle from 100% (no modulation) to 50% did not statistically alter the conversion values at either the top surface or at a depth of 2 mm when using a 10 second exposure of composite Z-100 (A2). With a 50% duty cycle and a 5 second exposure the conversion values were not statistically different at the top surface and only slightly lower at a 2 mm depth as compared to a 100% duty cycle. The addition of modulation at a 50% duty cycle reduced the intrapulpal temperature rise by approximate 27% for a 10 second exposure time.

While the present invention has been described with respect to the exemplary embodiments thereof, it will be recognized by those or ordinary skill in the art that many modifications may be made without departing from the spirit and scope of the invention. Therefore it is manifestly intended that the invention be limited only by the scope of the claims and the equivalents thereof.

We claim:

1. A light assembly for curing a photo-sensitive compound which comprises:

a curing lamp;

a curing lamp power supply;

an optic module for spectrally modifying illumination from said curing lamp;

an optical light guide for providing light energy from said curing lamp;

a control unit generating digital control voltage converted to analogue control voltage for providing constant current to said curing lamp;

means for inputting irradiation data for curing said photo-sensitive compound during a duty cycle; and for modulating light intensity between a maximum and minimum light intensity level during said duty cycle.

2. The light assembly for curing a photo-sensitive compound as defined in claim 1 wherein said control unit includes a micro-processor for generating said digital control voltage and an analogue converter integrated circuit for converting said digital control voltage to said analogue control voltage directed to said curing lamp power supply.

3. The light assembly for curing a photo-sensitive compound as defined in claim 2 wherein said light intensity is modulated on a constant basis by said micro-processor.

4. The light assembly for curing a photo-sensitive compound as defined in claim 2 wherein said light intensity is modulated in stepped form by said micro-processor.

5. The light assembly for curing a photo-sensitive compound in accordance with claim 2 and further including a light sensor for sensing light intensity from said optical light guide and providing an input signal to said micro-processor.

* * * * *